(12) United States Patent
Gasslander et al.

(10) Patent No.: US 8,691,869 B2
(45) Date of Patent: Apr. 8, 2014

(54) PHARMACEUTICAL FORMULATION OF NITROOXYDERIVATIVES OF NSAIDS

(75) Inventors: Ulla Gasslander, Sodertalje (SE); Christina Holmberg, Sodertalje (SE)

(73) Assignee: Nicox S.A., Sophia Antipolis (FR)

( * ) Notice: Subject to any disclaimer, the term of this patent is extended or adjusted under 35 U.S.C. 154(b) by 760 days.

(21) Appl. No.: 11/997,094

(22) PCT Filed: Jun. 29, 2006

(86) PCT No.: PCT/EP2006/063672
§ 371 (c)(1),
(2), (4) Date: Jul. 25, 2008

(87) PCT Pub. No.: WO2007/012539
PCT Pub. Date: Feb. 1, 2007

(65) Prior Publication Data
US 2009/0203759 A1 Aug. 13, 2009

(30) Foreign Application Priority Data
Jul. 26, 2005 (EP) .................................... 05106854

(51) Int. Cl.
A01N 37/00 (2006.01)
A61K 31/21 (2006.01)
C07C 229/00 (2006.01)
C07C 239/00 (2006.01)
C07C 259/00 (2006.01)

(52) U.S. Cl.
USPC ................ 514/509; 560/37; 560/43; 564/300

(58) Field of Classification Search
USPC ................ 514/509; 560/37, 43; 564/300
See application file for complete search history.

(56) References Cited

U.S. PATENT DOCUMENTS 5,874,106 A * 2/1999 Adesunloye et al. ......... 424/456

FOREIGN PATENT DOCUMENTS

| WO | WO 97/33568 A | 9/1997 |
| WO | WO 01/66087 A | 9/2001 |
| WO | WO 01/66088 A | 9/2001 |
| WO | WO 03/103582 A2 | 12/2003 |
| WO | WO 2004/010973 A2 | 2/2004 |

OTHER PUBLICATIONS

Singh, Saranjit, et al., "Alteration in Dissolution Characteristics of Gelatin-Containing Formulations, A Review of the Problem, Test Methods, and Solutions," Pharmaceutical Technology, Apr. 2002, pp. 36, 38, 40, 42, 44, 46, 48, 50, 52, 54, and 56.

* cited by examiner

Primary Examiner — Sarah Pihonak
(74) Attorney, Agent, or Firm — Arent Fox LLP

(57) ABSTRACT

The present invention relates to a pharmaceutical formulation comprising:
a) one or more NO-releasing NSAID(s) of formula (I);

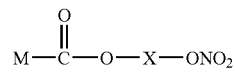

b) one or more surfactants;
c) a carbonyl scavenger compound selected from free acid forms, salts, carboxylic acid esters derivatives of a compound of formula (II)

$$H_2N-(CH_2)_m-(C_6H_4)-COOH \qquad (II)$$

wherein m=0-10; and
d) optionally an oil or semi-solid fat and/or a short-chain alcohol.

16 Claims, No Drawings

PHARMACEUTICAL FORMULATION OF NITROOXYDERIVATIVES OF NSAIDS

CROSS-REFERENCE TO RELATED APPLICATION

This application is a National Stage entry of International Application No. PCT/EP2006/063672, filed Jun. 29, 2006, the entire specification claims and drawings of which are incorporated herewith by reference.

The present invention relates to pharmaceutical formulations containing as active principle a nitrooxyderivative of NSAIDs, and their use for the preparation of gelatine capsules which exhibit reduce gelatine cross-linking.

Nitrogen oxide releasing non-steroidal anti-inflammatory drugs, commonly abbreviated NO-releasing NSAIDs, have recently been found have a good anti-inflammatory activity and an improved side-effect profile such as they show a better gastric tolerability than the commercially available NSAIDs, see e.g. WO 94/04484, WO 94/12463, WO 95/09831 and WO 95/30641.

NO-releasing NSAIDs are lipophilic compounds with poor aqueous solubility. A biopharmaceutical problem with these compounds is that their absorption from the gastrointestinal tract (GIT) may be dissolution rate limited, resulting in poor bioavailability upon oral administration.

EP 1267832 and WO 0166087 disclose pharmaceutical compositions suitable for oral administration in form of an emulsion pre-concentrate comprising one or more NO-releasing NSAID; said composition can be filled into single unit dosage forms such as capsules, drinking ampoules and dose cushions.

The disclosed pharmaceutical formulations upon contact with aqueous media, such as gastrointestinal fluids or water, form an oil-in-water emulsion that provides a good bioavailability of the NO-releasing NSAID.

It has been found that gelatine capsules containing the pharmaceutical composition described in the above reported documents suffer from retardation of disintegration and dissolution with the passage of time and/or under accelerate storage conditions (high humidity and or high temperature) or in customary packaging. These changes in the dissolution rate of the dosage form results in a delayed release of NO-realising NSAIDs contained in the capsules and in a potential alteration of the in in vivo dissolution and bioavailability of the drug. A considerably delayed disintegration time of the gelatine capsule is not acceptable because a high drug release rate and consequently a fast absorption of the active principle is important since the NO-releasing NSAIDs are used in the treatment of pain and/or inflammation and a fast action is required.

The delayed disintegration and dissolution is due to the chemical modification of the crosslinked capsule shells and to its consequent physical modification. The gelatine becomes hard, but brittle, with risk of break of the shells. In addition these changes of the dosage form result in a delayed release of NO-releasing NSAIDs contained in the capsules and in a potential alteration of the in vivo dissolution and bioavailability of the drug.

As a consequence of the above reported considerations, the undesired cross-linking of gelatine capsules containing NO-releasing NSAIDs should be avoided.

Drug Development and Industrial Pharmacy, 24(6), 493-500 (1998) reports that the alteration of the gelatine capsules is thought to result from cross-linking of gelatine chains. One of the possible causes of cross-linking of gelatine capsule is the presence in the encapsulated pharmaceutical formulation of substances such as, for example, aldehydes (glutaraldehyde, formaldehyde, glyceraldehydes) glucose, hydrogen peroxide, benzene, sulfonic acid ecc. that can be formed by the auto-oxidation of the excipients or can be present as impurities.

In literature are reported several compounds effective to prevent gelatine capsules cross-linking; these inhibitors include semicarbazide hydrochloride, hydroxylamine, pyridine, piperidine, glycerine and p-aminobenzoic acid. In particular amines are reported to be effective to prevent cross-linking in gelatine in fact, by acting as "carbonyl scavengers", amines are able to reduce the concentration of aldehydes.

WO2004/010973 describes pharmaceutical dosage form comprising a fill material sealed in a gelatine capsule; the fill material comprises a selective COX-2 inhibitory drug of low solubility, and a primary or secondary amine in an amount sufficient to inhibit cross-linking of gelatine capsule upon storage of the dosage form. The preferred primary or secondary amine compounds disclosed in the document are for example tromethamine, ethanolamine, ethylenediamine, l-arginine, l-lysine, diethanolamine, benethamine, benzathine.

The application provides dosage form having a decreased gelatine cross-linking, but it does not mention the problem of the chemical interaction between the active principle and the amine agent and the consequently degradation of the drug.

WO 03/103582 relates to methods for reducing cross-linking in the gelatine shell of gelatine capsules containing hydrophilic and lipophilic fillings, in particular the document discloses the incorporation of a free amino acid into the capsule shell optionally in combination with the inclusion of an ester of carboxylic acid either into the capsule filling and/or into the lubricant agent.

Among the amino acids mentioned in the document p-aminobenzoic acid or its salts are cited.

The present invention is based on the unexpected and surprising found that among the "carbonyl scavengers" of the group of the aminocarbonylic compounds, p-aminobenzoic acid or its esters inhibits the cross-linking of the gelatine capsule shell of the gelatine capsules containing NO-releasing NSAIDs without inducing the degradation of the molecule of the active principle.

It is an object of the present invention pharmaceutical formulations comprising:
a) one or more NO-releasing NSAID(s) of formula (I);

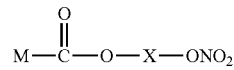

b) one or more surfactants, preferably a non-ionic surfactants, wherein the ratio surfactant: NO-releasing is from 0.1:1 to 10:1, preferably from 0.3:1 to 3:1;
c) a carbonyl scavenger compound selected from free acid forms, salts, carboxylic acid esters derivatives of a compound of formula (II)

$$H_2N-(CH_2)_m-(C_6H_4)-COOH \qquad (II)$$

wherein m=0-10, preferably m is 0; preferably the component c) is p-aminobenzoic acid (PABA), wherein the amount is from about 0.01% to about 5% by weight of the total weight of the composition, preferably in an amount of from about 0.01% to about 2% by weight of the total weight of the composition, more preferably in an amount of from about 0.01% to about 1% by weight of the total weight of the composition, most preferably in an amount of 0.1% or 0.5% by weight of the total weight of the composition;

d) optionally an oil or semi-solid fat and or an a short-chain alcohol;

wherein in formula (I)

M is selected from the group consisting of

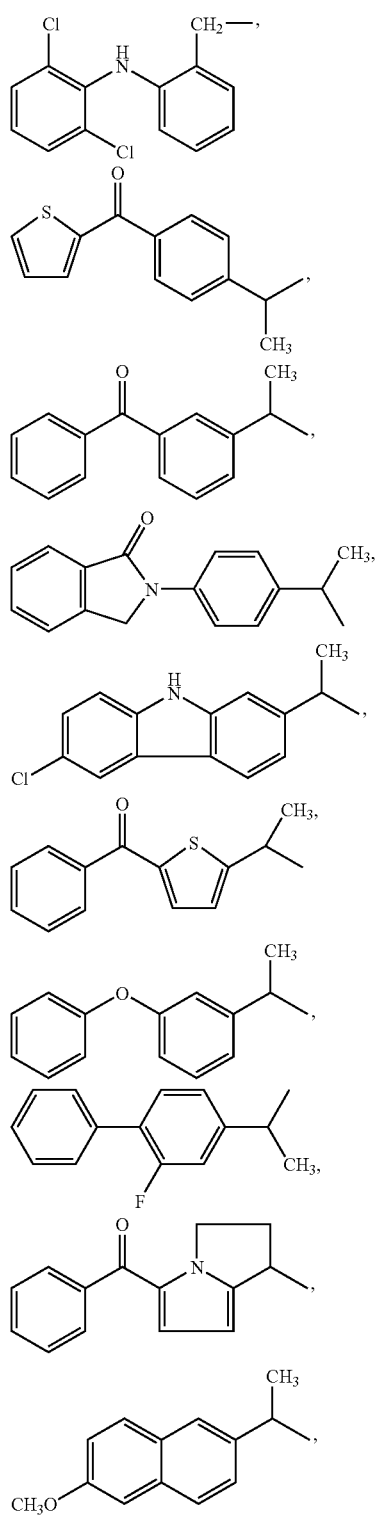

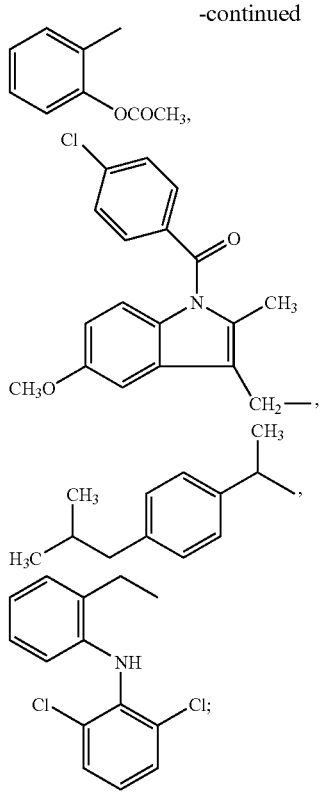

X is a spacer, i.e. a compound forming a bridge between the nitrogen oxide donating group and the NSAID, and is selected from i) straight or branched $C_1$-$C_{20}$ alkylene, preferably $C_1$-$C_{10}$, being optionally substituted with one or more of the substituents selected from the group consisting of: halogen atoms, hydroxy, —$ONO_2$ or T, wherein T is —$OC(O)(C_1$-$C_{10}$ alkyl)-$ONO_2$ or —$O(C_1$-$C_{10}$ alkyl)-$ONO_2$;

ii) $C_5$-$C_7$ cycloalkylene group optionally substituted with linear or branched $C_1$-$C_{10}$ alkyl group, preferably $CH_3$;

iii)

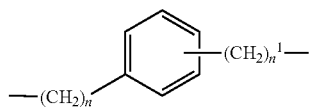

wherein n is an integer from 0 to 20, preferably n is an integer from 0 to 5; and $n^1$ is an integer from 1 to 20, preferably $n^1$ is an integer from 1 to 5; with the proviso that the —$ONO_2$ group of formula (I) is bound to —$(CH_2)_{n^1}$; and iv)

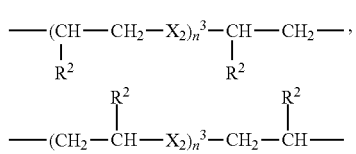

wherein $X_2$ is —O— or —S—;

$n^3$ is an integer from 1 to 6, preferably from 1 to 4, and $R^2$ is H or $CH_3$;

The wording "carbonyl scavenger" refers to primary amine derivatives of benzoic acid capable of covalently reacting with the carbonyl substance such as aldehydes.

The wording "surfactant" is defined as surface-active amphiphilic compounds such as block co-polymers. Preferred surfactants in accordance with the present invention are non-ionic surfactants, for example those containing polyethylene glycol (PEG) chains, particularly block co-polymers such as poloxamers.

Examples of suitable poloxamers are Poloxamer 407 (Pluronic F127®); Poloxamer 401 (Pluronic L121®); Poloxamer 237 (Pluronic F87®); Poloxamer 338 (Pluronic F138®); Poloxamer 331 (Pluronic L101®); Poloxamer 231 (Pluronic L81®); tetrafunctional polyoxyethylene polyoxypropylene block copolymer of ethylene diamine, known as Poloxamine 908 (Tetronic 908®); Poloxamine 1307 (Tetronic 1307®); Poloxamine 1107 polyoxyethylene polyoxybutylene block copolymer, known as Polyglycol BM45®.

This list is only intended to serve as exemplification of surfactants that may be used in accordance with the present invention, and should not in any way be considered as exhaustive or as limiting the invention.

All surfactants described above are commercially available from e.g. BASF, Dow Chemicals, and Gattefossé. The pharmaceutical compositions of the invention are suitable for preparing pharmaceutical dosage form comprising soft and hard gelatine capsules.

The wording "pharmaceutical dosage" form is use for defining unit dose comprising an amount of active compound administered in one single capsule, or dissolved in one glass of water.

The total amount of NO-releasing NSAID(s) used in the pharmaceutical dosage form of the invention is preferably in the range 50-1500 mg per unit dose. In still a further preferred embodiment, the amount of NO-releasing NSAID(s) used in the composition is 125-800 mg per unit dose.

The total amount of surfactant(s) per unit dose may be within the range of from 12.5-2000 mg, preferably of from 100-500 mg.

Additionally, a pharmacologically inert oil or semisolid fat may be added to the pharmaceutical composition by means of as filler or as a viscosity regulator. A filling agent may be required to increase dosing accuracy for low dose compounds. A viscosity regulator may be required in order to adjust optimal viscosity for filling of the composition into e.g. capsules. In particular high-speed liquid filling of capsules requires careful adjustment of viscosity within a range that prevents splashing on the low viscosity end and thread-formation on the high viscosity end. Moreover, the viscosity range must be chosen so as to give a pumpable formulation. The viscosity range typically required for liquid filling of capsules is from 0.1 to 25 Pa s.

If additional oil is added to the pharmaceutical composition this may be any oil as long as it is inert and compatible with the capsule material, as well as being acceptable for use in pharmaceuticals. A person skilled in the art will appreciate which oil to select for the intended purpose. Examples of suitable oils that may be used in accordance with the present invention are vegetable oils such as coconut oil, corn oil, soybean oil, rapeseed oil, safflower oil and castor oil. Also animal oils such as fish oil and triglycerides are suitable for the purposes of the present invention.

If a semi-solid fat is used as a filler for the pharmaceutical composition, this may preferably be selected from mono-, di- and triglycerides, and fatty acid alcohol such as stearyl alcohol, Gelucires 33/01®, 39/01®, 43/01®, glyceryl palmitostearate such as Precirol ATO5®. Gelucire is a mixture obtained by mixing mono-, di-, and trimesters of glycerol, mono- and di-esters of PEG, or free PEG.

The wording "short-chain alcohols" used in accordance with the present invention is herein defined as linear or branched mono-, di- or tri-alcohols having 1-6 carbon atoms. Examples of such short-chain alcohols useful in accordance with the invention are ethanol, propylene glycol and glycerol.

If a short-chain alcohol is added to the pharmaceutical composition according to the invention, the solubility is enhanced and a smaller amount of surfactant is required.

In a preferred embodiment of the invention, the NO-releasing NSAIDs is selected from the group consisting of:

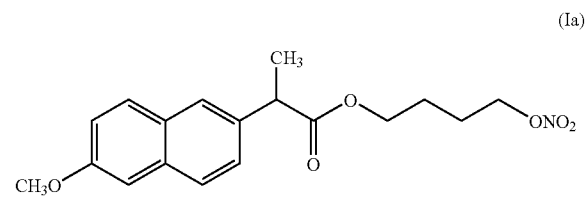

(Ia)

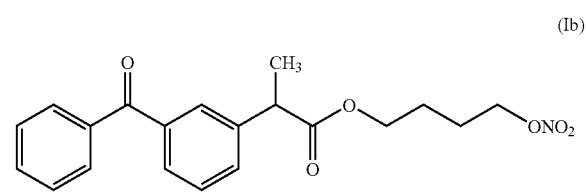

(Ib)

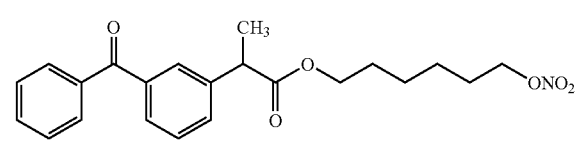

(Ic)

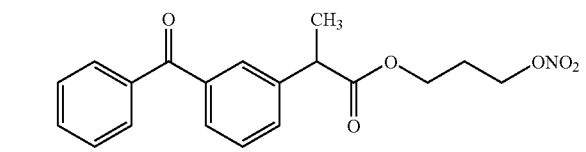

(Id)

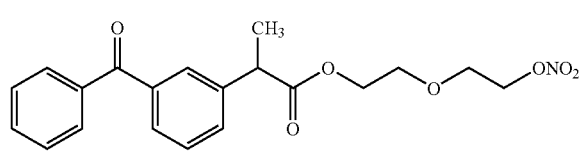

(Ie)

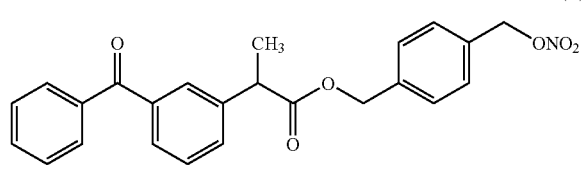

(If)

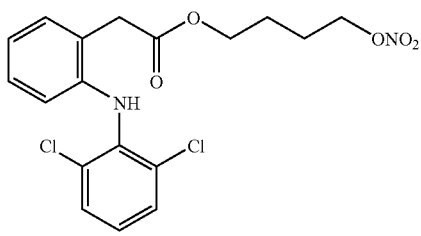 (Ig)

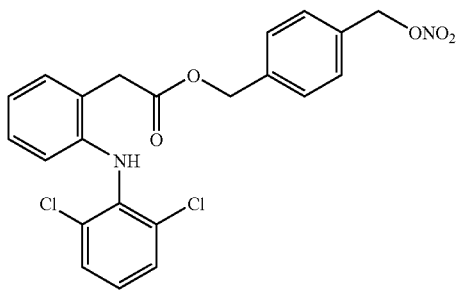 (Ii)

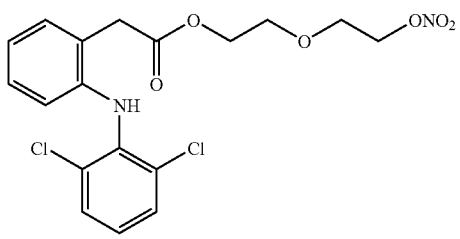 (Ij)

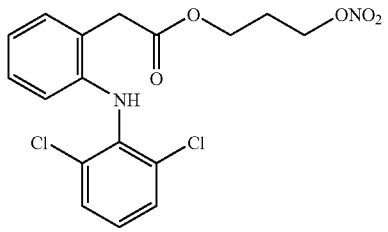 (Ik)

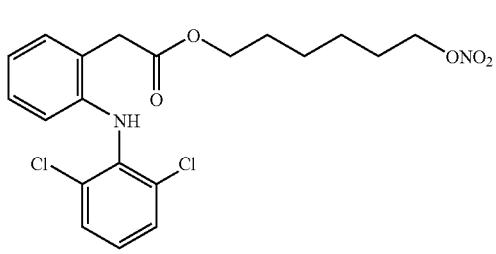 (IL)

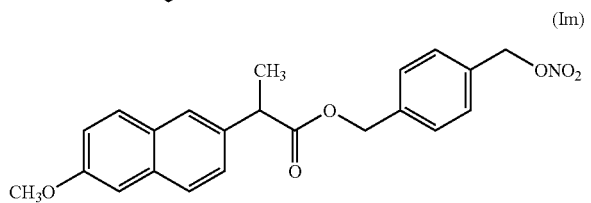 (Im)

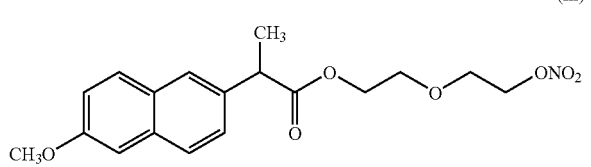 (In)

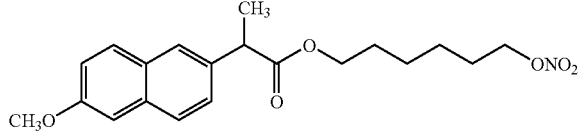 (Io)

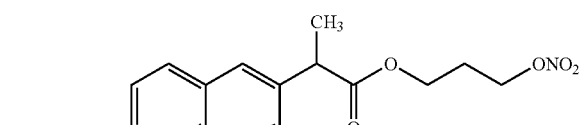 (Ip)

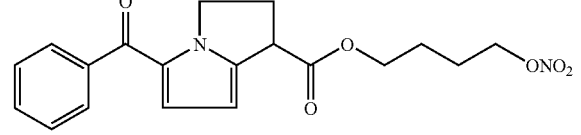 (Iq)

A typical composition of the invention comprises:

a) a NO-releasing NSAID selected from the group of compounds of formula (Ia)-(Iq);

b) one or more non-ionic surfactant(s) selected from the group of the block-copolymers, wherein the ratio surfactant: NO-releasing is from 0.1:1 to 10:1, preferably from 0.3:1 to 3:1;

c) p-aminobenzoic acid (PABA) in an amount of from about 0.01% to about 5% by weight of the total composition, preferably in an amount of from about 0.01% to about 2% by weight of the total weight of the composition, more preferably in an amount of from about 0.01% to about 1% by weight of the total weight of the composition.

d) optionally an oil or semi-solid fat and or an a short-chain alcohol;

Another preferred composition of the invention comprises:

a) a NO-releasing NSAID of formula (Ia)

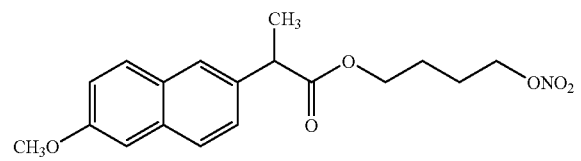

b) one or more non-ionic surfactant(s) selected from the group of the block-copolymers, wherein the ratio surfactant(s):compound of formula (Ia) is from 0.1:1 to 10:1, preferably in a ratio from 0.3:1 to 3:1;

c) para-aminobenzoic acid (PABA), in an amount of from about 0.01 to about 2% by weight of the total composition, more preferably in an amount of from about 0.01% to about 1% by weight of the total weight of the composition;

d) optionally an oil or semi-solid fat and or an a short-chain alcohol;

Another preferred composition of the invention comprises:
a) a NO-releasing NSAID of formula (Ia)

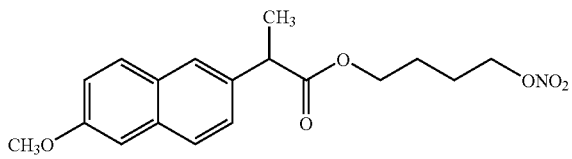

b) one or more non-ionic surfactant(s) selected from the group of the poloxamers, wherein the ratio surfactant(s): compound of formula (Ia) is from 0.3:1 to 3:1;
c) para-aminobenzoic acid (PABA), in an amount of from about 0.01% to about 0.5% by weight of the total weight of the composition, most preferably in an amount of 0.1% or 0.5% by weight of the total weight of the composition;
d) optionally an oil or semi-solid fat and or an a short-chain alcohol.

In another aspect of the invention, two or more NO-releasing NSAIDs are used as active ingredients, where anyone of said drugs may be present as an oil or as a semi-solid, or where at least one of said drugs is present as an oil or as a semi-solid and the other one(s) may be present as a solid which is dissolved or suspended in the oily or semi-solid compound. Combinations of two or more NO-releasing NSAIDs may be advantageous in case of a high-dose low potent NO-releasing NSAID is desired to be supplemented with a low dose of a high potent NO-releasing NSAID.

Experimental Part

Compounds of formula (I) can be prepared as described in WO 94/04484, WO 94/12463, WO 95/09831 and WO 95/30641, which are hereby incorporated by reference.

4-aminobenzoic acid (PABA) is commercially available, General Procedure for Preparing the Composition of the Invention and the Gelatine Capsules
a) Preparation of the Composition of the Invention The drug substance is weighed into a thermostatic stainless steel vessel and eventually heated. 4-aminobenzoic acid (PABA) or p-aminoalkylbenzoic acid is then added. The formulation is stirred until the full dissolution of PABA or p-aminoalkylbenzoic acid. Surfactant and optionally one or more oil are then added and the mixture is stirred.
b) Preparation of the Gelatin Capsules The bulk solution should be stirred and kept at a temperature that permits to have a viscosity suitable for the capsule filling. The melted mixture is filled into hard gelatine capsules. The filling operation is performed with a standard automatic capsule-filling machine.

EXAMPLE 1

Compound of formula (Ia) (93.75 g) was weighed into a thermostatic stainless steel vessel and heated to a temperature of 62° C. p-aminobenzoic acid (PABA) (0.15 g) is then added. The formulation is stirred until the full dissolution of PABA. Poloxamer 407 (56.1 g) is then added and the mixture is stirred, always at a temperature not exceeding 62° C.
Preparation of the Dosage Form: Hard Gelatin Capsules The melted mixture is filled into hard gelatine capsules (250 units). The bulk solution should be stirred and kept at a temperature that permits to have a viscosity suitable for the capsule filling. The temperature of the mixture should not exceed 62° C. The filling operation is performed with a standard automatic capsule-filling machine.

Sealing: The filled capsules are sealed, by spraying a solution of water/ethanol onto the capsule. The sealing solution is then evaporated by air treatment while the capsules pass through a rotating tunnel with airflow of about 45° C.

EXAMPLE 2

Comparison of Dissolution Profile of a Formulation Containing Compound of Formula (Ia) with and without p-Aminobenzoic Acid (PABA)

The dissolution profile of capsules containing a formulation of the invention (dosage form A) and of capsules filled with a formulation not containing p-amino benzoic acid (PABA) (dosage form B) was tested after 3 months at 40° C./75% RH.

The two formulations were prepared as described in example 1 and the composition of the two formulations are reported in the table 1:

TABLE 1

| Dosage form | Formulation without PABA B) Hard gelatine capsule | | Formulation with PABA A) Hard gelatine capsule | |
|---|---|---|---|---|
| Formulations | Compound (Ia) | 375 mg | Compound (Ia) | 375 mg |
| | Poloxamer 407 | 225 mg | Poloxamer 407 | 225 mg |
| | | | PABA (0.5%) | 3 mg |

Dissolution Test Conditions

The test was performed with the following apparatus and conditions:
Apparatus: USP apparatus 2 (Paddle method), Sotax AT7
Medium: 1000 ml phosphate buffer pH 6.8+8.8 g cetyltrimethylammonium bromide (CTAB)
Speed: 75 rpm
Temperature: 37±0.5° C.
Absorbance is measured with an UV detector at 273 nm with the following frequency: 20, 40, 60, 80 min.

The results reported in table 2 of the dissolution test show that the dissolution profile of the capsules containing the formulation of the invention was improved after 3 months at 40° C./75% RH and in vitro dissolution showed not sign of being delayed due to cross linking. Table 2: (n=3)

TABLE 2

| Minutes | % Dissolved Dosage form A) Capsule with PABA | % Dissolved Dosage form B) Capsule without PABA |
|---|---|---|
| 20 | 18 | Below detection limit |
| 40 | 52 | <5 |
| 60 | 83 | 5 |
| 80 | 100 | 6 |

EXAMPLE 3

Three amines were selected as test compounds based on their solubility and compatibility with the formulation:
one primary aliphatic amine: 4-amino-1-butanol
one secondary aliphatic amine: diethanol amine
one primary aromatic amino acid: 4-aminobenzoic acid (PABA).

A set of 4 formulations was prepared in 20 g scale containing 2.5% of the total weight of the batch the above reported amines as additives and a reference formulation without the additive was also prepared:
batch 1: 4-amino-1-butanol,
batch 2: diethanol amine and
batch 3: p-amino-benzoic acid,
batch 4: a reference formulation.

The formulations were prepared as follows: Compound of formula (Ia) (12.2 g) was weighed into a thermostatic stainless steel vessel and heated to a temperature of 62° C. The amine (0.5 g) is then added. The formulation is stirred until the full dissolution of the amine. Poloxamer 407 (7.3 g) is then added and the mixture is stirred, always at a temperature of 62° C.

The melted mixture is filled into hard gelatine capsules (33 units). The bulk solution should be stirred and kept at a temperature that permits to have a viscosity suitable for the capsule filling. The filling operation is performed with a standard automatic capsule-filling machine.

Sealing: The filled capsules are sealed, by spraying a solution of water/ethanol onto the capsule. The sealing solution is then evaporated by air treatment while the capsules pass through a rotating tunnel with airflow of about 45° C.

The capsules were placed at 40° C./75% RH for 1 month and tested for disintegration and total organic impurities related to the compound (Ia).

The results reported in Table 3 indicated that the two aliphatic amines generated unacceptable levels of impurities/reaction products.

TABLE 3

| Batch | Amine | Disintegration (minutes) | Total organic impurities |
|---|---|---|---|
| 1 | 4-amino-1-butanol | 10 | 11 |
| 2 | diethanol amine | >20* | 7.7 |
| 3 | p-amino-benzoic acid | 9 | 0.7 |
| 4 | reference | 9 | 0.4 |

*not completely dissolved at 20 min, veil remaining

The invention claimed is:

1. A gelatin capsule comprising a filling, the filling consisting essentially of:

a) one or more NO-releasing NSAID(s) of formula (I)

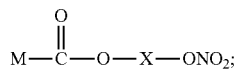
(I)

b) one or more surfactants wherein the ratio of surfactant to NO-releasing NSAID is from 0.1:1 to 10:1;

c) a carbonyl scavenger compound selected from the group consisting of: free acid forms, salts, and carboxylic acid esters derivatives of a compound of formula (II)

(II)

wherein m=0-10, wherein the amount of the compound of formula (II) is from about 0.01% to about 5% by weight of the total weight of the composition;

wherein in formula (I)

M is selected from the group consisting of:

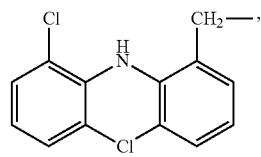

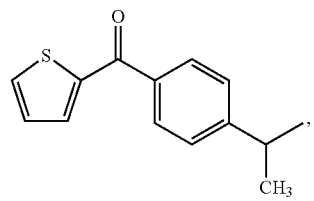

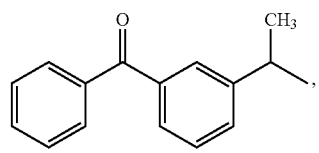

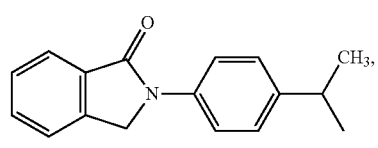

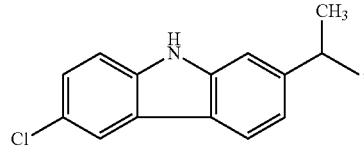

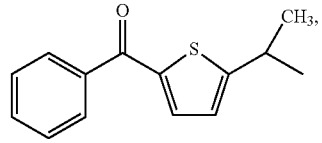

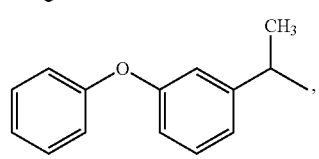

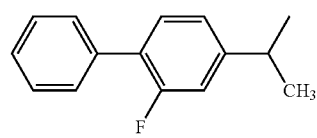

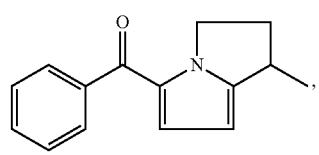

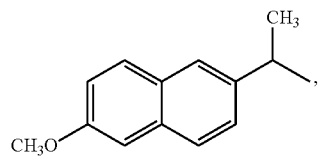

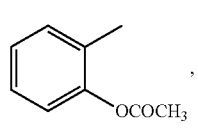

-continued

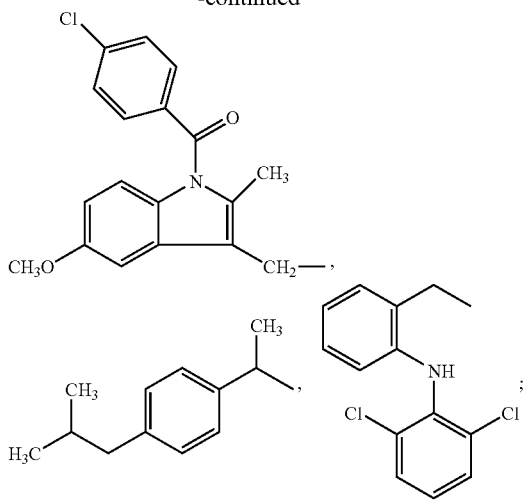

X is a spacer selected from the group consisting of:
i) straight or branched $C_1$-$C_{20}$ alkylene being optionally substituted with one or more of the substituents selected from the group consisting of: halogen atoms, hydroxy, —$ONO_2$ and T, wherein T is —OC(O)($C_1$-$C_{10}$ alkyl)-$ONO_2$ or —O($C_1$-$C_{10}$ alkyl)-$ONO_2$;
ii) $C_5$-$C_7$ cycloalkylene group optionally substituted with linear or branched $C_1$-$C_{10}$ alkyl group;
iii)

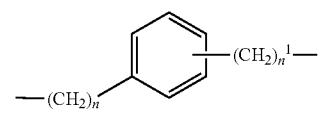

wherein n is an integer from 0 to 20; and
$n^1$ is an integer from 1 to 20; wherein the —$ONO_2$ group of formula (I) is bound to —$(CH_2)_{n^1}$; and
iv)

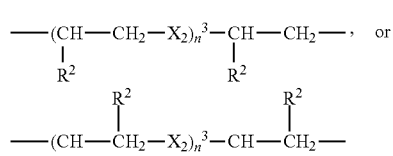

wherein
$X_2$ is —O— or —S—;
$n^3$ is an integer from 1 to 6, and $R_2$ is H or $CH_3$.

2. The pharmaceutical formulation according to claim 1 wherein the amount of the compound of formula (II) is from about 0.01% to about 2% by weight of the total weight of the composition.

3. The pharmaceutical formulation according to claim 1 wherein the amount of the compound of formula (II) is from about 0.01% to about 1% by weight of the total weight of the composition.

4. The pharmaceutical formulation according to claim 1, wherein the ratio of surfactant to NO-releasing NSAID is from 0.3:1 to 3:1.

5. The pharmaceutical formulation according to claim 1, wherein the surfactant is non-ionic.

6. The pharmaceutical formulation according to claim 5, wherein the surfactant is a poloxamer.

7. The pharmaceutical formulation according to claim 1, wherein the compound of formula (II) is p-aminobenzoic acid.

8. The pharmaceutical formulation according to claim 1 wherein the NO-releasing NSAID of formula (I) is selected from the group consisting of:

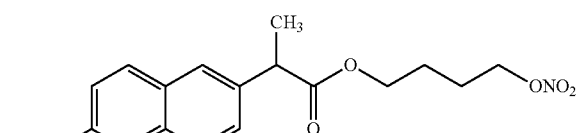
(Ia)

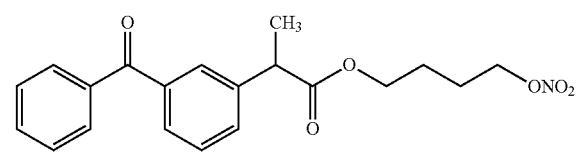
(Ib)

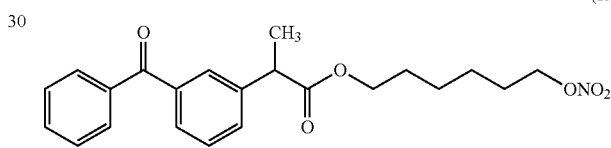
(Ic)

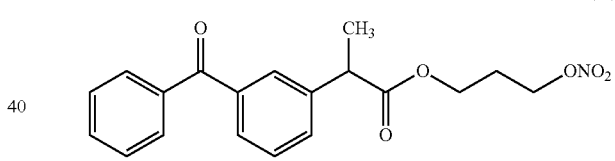
(Id)

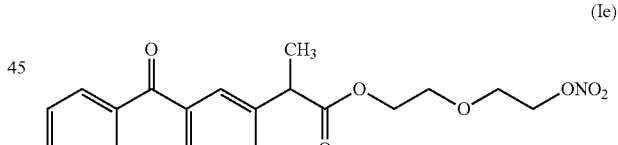
(Ie)

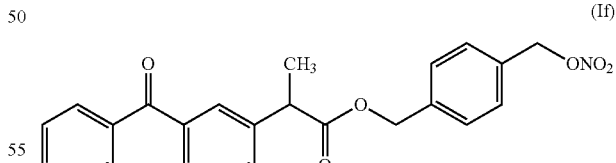
(If)

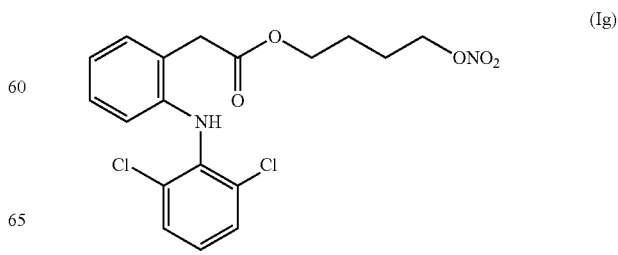
(Ig)

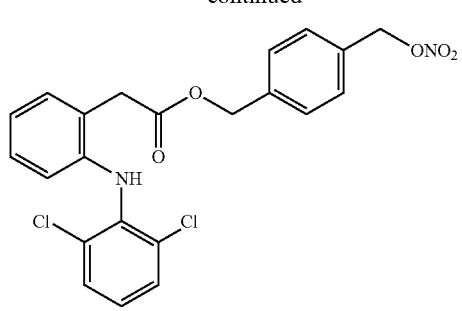 (Ii)

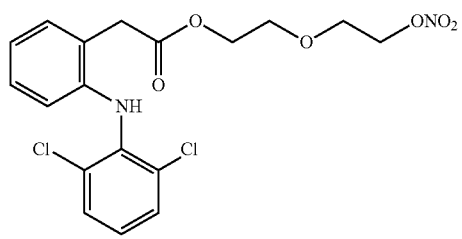 (Ij)

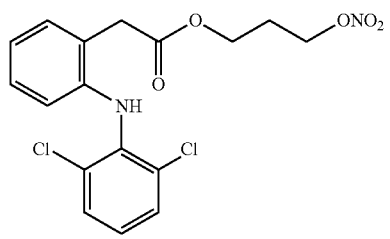 (Ik)

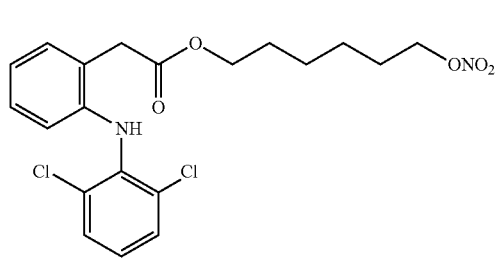 (IL)

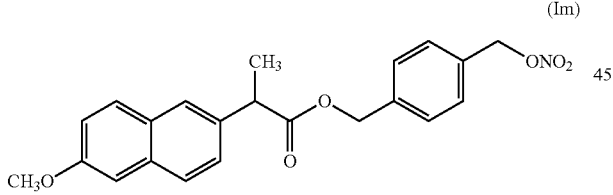 (Im)

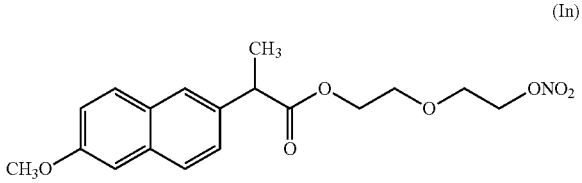 (In)

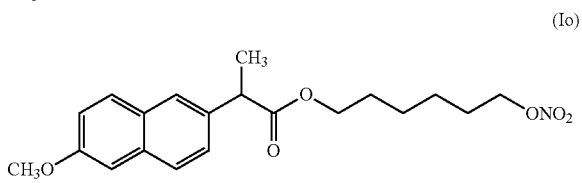 (Io)

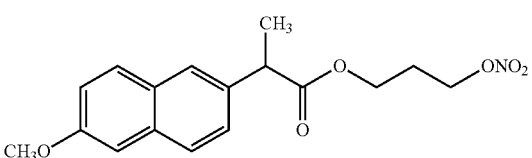 (Ip)

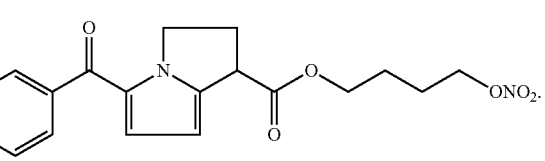 (Iq)

9. The pharmaceutical formulation according to claim 1 wherein the NO-releasing NSAID of formula (I) is the compound of formula (IA)

(Ia)

10. The pharmaceutical formulation according to claim 9 wherein
   b) the surfactant is poloxamer 407 and the ratio of surfactant to compound (Ia) is 0.6; and
   c) the compound of formula (II) is p-aminobenzoic acid and the amount of p-aminobenzoic acid is about the 0.1% by weight of the total weight of the composition.

11. The pharmaceutical formulation according to claim 9 wherein
   b) the surfactant is poloxamer 407 and the ratio of surfactant to compound (Ia) is 0.6; and
   c) the compound of formula (II) is p-aminobenzoic acid and the amount of p-aminobenzoic acid is about the 0.5% by weight of the total weight of the composition.

12. The pharmaceutical formulation according to claim 1, wherein X is a straight or branched $C_1$-$C_{10}$ alkylene, being optionally substituted with one or more of the substituents selected from the group consisting of: halogen atoms, hydroxy, —$ONO_2$ and T, wherein T is —OC(O)($C_1$-$C_{10}$ alkyl)-$ONO_2$ or —O($C_1$-$C_{10}$ alkyl) —$ONO_2$.

13. The pharmaceutical formulation according to claim 1, wherein X is a $C_5$-$C_7$ cycloalkylene group optionally substituted with $CH_3$.

14. The pharmaceutical formulation according to claim 1, wherein n is an integer from 0 to 5.

15. The pharmaceutical formulation according to claim 1, wherein $n^1$ is an integer from 1 to 5.

16. The pharmaceutical formulation according to claim 1, wherein $n^3$ is an integer from 1 to 4.

* * * * *